United States Patent
Bhonde et al.

(10) Patent No.: US 7,074,433 B2
(45) Date of Patent: Jul. 11, 2006

(54) PROCESS FOR THE CURE AND CONTROL OF DIABETES MELLITUS USING NATURAL PRODUCTS FROM PERNA VIRIDIS

(75) Inventors: Ramesh Ramchandra Bhonde, Pune (IN); Anil Chatterji, Goa (IN)

(73) Assignees: Council of Scientific and Industrial Research, New Delhi (IN); Department of Biotechnology, new Delhi (IN)

( * ) Notice: Subject to any disclaimer, the term of this patent is extended or adjusted under 35 U.S.C. 154(b) by 714 days.

(21) Appl. No.: 10/112,078

(22) Filed: Mar. 29, 2002

(65) Prior Publication Data

US 2002/0187201 A1 Dec. 12, 2002

Related U.S. Application Data

(60) Provisional application No. 60/280,077, filed on Mar. 30, 2001.

(51) Int. Cl.
*A61K 35/56* (2006.01)

(52) U.S. Cl. ...................................................... 424/547
(58) Field of Classification Search .................. 424/547
See application file for complete search history.

*Primary Examiner*—Brenda Brumback
*Assistant Examiner*—Randall Winston
(74) *Attorney, Agent, or Firm*—Ladas & Parry

(57) ABSTRACT

The present invention relates to a process for the cure and control of Diabetes mellitus using natural products isolated from *Perna viridis*.

21 Claims, No Drawings

PROCESS FOR THE CURE AND CONTROL OF DIABETES MELLITUS USING NATURAL PRODUCTS FROM *PERNA VIRIDIS*

This application claims the benefit of provisional application No. 60/280,077, filed Mar. 30, 2001.

FIELD OF THE INVENTION

The present invention relates to a process for the cure and control of Diabetes mellitus using natural products isolated from *Perna viridis*. More particularly, the present invention relates to a process for the cure and control of Diabetes mellitus using natural products from *Perna viridis*.

BACKGROUND OF THE INVENTION

The birth and death of Pancreatic β-cells is of obvious importance to the cure of Diabetes mellitus. For many years, β-cells were considered terminally differentiated and unchanging after birth. However, based on the experimental animal models, the concept that β-cell mass is not static but dynamic with ability to compensate for maintenance of glucose homeostasis has been proposed. In this context, search for the factors that lead to direct differentiation of β-cells from precursor β-cell mass in the diabetic individual is important to find out novel approaches to control and cure of diabetes by natural products obtained from the Indian marine bivalves *Perna viridis*.

The tissue extract from cellophan wrapped pancreas has been shown to possess trophic activity on pancreatic tissue inducing islet cell regeneration[1]. The active compound of cellophane wrapped pancreatic extract which is called as 'ilotropin' has also been shown to be effective in reversal of Streptozotocin induced diabetes by induction of islet neognesis[2]. The regenerating pancreas is being shown to posses islet neogenetic activity leading to reversal of experimental diabetes[3]

The process of preparation of extract was developed for the first time by the Russian scientists. A patent was also filed on a process developed by Russian scientists vide Patent No. RU 2043109. The extract prepared from the Indian green mussel (*Perna viridis*) has previously been found to be active against all influenza, herpes and hepatitis viral strains. The extract is also found to possess not only prophylactic efficacy for protection from several viral diseases but it also shows a high therapeutic activity against these diseases. The process of preparation of extract was developed by NIO, Goa, in collaboration with the Russian Scientists.

The tissue extract from cellophane wrapped pancreas has been shown to possess trophic activity on pancreatic tissue inducing islet cell regeneration (Rosenberg L. and Vinik, A. I. 1989, Induction of endocrine cell differentiation: A new approach to management of diabetes, *J. Lab. Clin. Med.*, 114:75–83). The active compound of cellophane wrapped pancreatic extract called as 'ilotropin' has also been shown to be effective in reversal of streptozotocin induced diabetes by induction of islet neognesis (Rosenberg, L. Duguid, W. P. Healy, M. Clas, D. and Vinik, A. I. 1992, Reversal of diabetes by the induction of islet cell neogenesis, *Transplant Proc.*, 24: 1027–1028). The regenerating pancreas is being shown to possess islet neognesis activity leading to reversal of experimental diabetes (Hardikar, A. A. and Bhonde, R. R., 1999, Modulating experimental diabetes by treatment with cytosolic extract from the regenerating pancreas, *Diabet. Res. Clin. Pract*, 46: 203–211).

OBJECT OF THE INVENTION

Accordingly it is an object of the invention to eliminate the need to use pancreatic preparations from animals for the reversal of diabetes.

It is another object of the invention, to assess the islet protecting activity of the mussel hydrolysate.

It is another object of the invention to determine the hypoglycemic and islet neogensis activity of the hydrolysate.

SUMMARY OF THE INVENTION

The invention provides a process for the cure and control of Diabetes mellitus using natural products from *Perna viridis*.

The present invention relates to the use of an extract of Indian green mussel for cure of diabetes mellitus due to the hypoglycemic activity and pancreatic regeneration potential of the extract prepared from the green mussel, said use comprising diluting extract by 50 times with 1×PBS, adjusting the pH to 7.2, adding extract to mouse islet cultures, injecting the extract to STZ diabetic mice and observing the blood glucose level of treated and untreated mice to ensure hypoglycemic activity.

The invention also relates to the use of natural products from *Perna viridis* for the cure and control of Diabetes mellitus.

In one embodiment of the invention, the extract permits elimination of pancreatic preparation from the animals, examination of the role of putative factors from the extract in preventing β-cell apoptosis and evaluation of the mechanisms of action of the extract probably in curing diabetes.

In another embodiment of the present invention, hypoglycemic activity and pancreatic regeneration potential of the extract prepared from the green mussel is done with diluting the extract with 1×PBS by 50 times.

In another embodiment of the invention, the pH of the extract is adjusted to 7.2 with alkali (1 N NaOH)

In a further embodiment of the invention, the islets isolated from the mouse pancreas are cultured in six well plate in presence of RPMI-1640 supplemented with 10% diluted extract.

In a further embodiment of the invention, six well plates are incubated in a $Co_2$ incubator at 37° C. for 15 to 30 days to determine the viability integrity and attachment of the islets to the plates.

In another embodiment of the invention, the mussel hydrolysate has high protein content and contains no glucose.

In another embodiment of the invention, the mussel hydrolysate supports attachment and proliferation of AR42J cell line (pancreatic adenocarcinoma cell line) in a very low concentration (dilution 1:800 and 1:400) and in absence of FCS.

In a further embodiment of the invention, the mussel hydrolysate maintains the viability of pancreatic acinar cells.

In a further embodiment of the invention, 0.2 ml of extract is injected with the help of a sterilized disposable syringe to STZ induced diabetic mice.

In a further embodiment of the invention, the blood glucose level of treated and untreated mice is estimated using a glucometer to check hypoglycemic activity.

DETAILED DESCRIPTION OF THE INVENTION

According to the present invention, a process for the cure and control of Diabetes mellitus using natural products from *Perna viridis* has been found to be non-toxic and cytoprotective to isolated Islets of Langerhans from mouse pancreas. The extract is also found to posses islet neogenesis activity as evidenced by the reversal of the experimental diabetes in mice.

Preparation of Extract Marine Bivalves:

Live green mussels collected from the natural environment were deshelled and meat and mantle fluid was removed. The mixture of mantle fluid and meat was fermented at 40° C. for two hours, the distillation and digestion process was carried out with concentration hydrochloric acid at 100+5° C. for 20 hours. The resultant solution was neutralized with an alkali at room temperature to achieve a pH of 5.6 The active extract was isolated by keeping the solution in a separating flask and carefully removing the middle part of the solution after allowing the extract for settlement for 15 days.

Methodology

Hypoglycemic activity and pancreatic regeneration potential of the extract prepared from the green mussel was done by diluting the extract with 1×PBS by 50 times. The pH of the extract is adjusted to 7.2 with alkali (1 N NaOH).

The islets isolated from the mouse pancreas are cultured in six well plate in presence of RPMI-1640 supplemented with 10% diluted extract. The well plates are incubated in a $CO_2$ incubator 37° C. for 15 to 30 days to see the viability integrity and attachment of the islets to the plates. The 0.2 ml of extract is injected with the help of a sterilized disposable syringe to STZ diabetic mice.

The blood glucose level of treated and untreated mice is estimated using glucometer to check hypoglycemic activity.

EXAMPLE

Live green mussels collected from the natural environment were deshelled and meat and mantle fluid was removed. The mixture of mantle fluid and meat was fermented at 40° C. for two hours, The distillation and digestion process was carried out with concentrated hydrochloric acid at 100+5° C. for 20 hours. The resultant solution was neutralized with an alkali at room temperature to achieve a pH of 5.6. The active extract was isolated by keeping the solution in a separating flask and carefully removing the middle part of the solution after allowing the extract for settlement for 15 days.

The hypoglycemic activity and pancreatic regeneration potential of the extract prepared from the green mussel is done with diluting the extract with 1×PBS by 50 times. The pH of the extract is adjusted to 7.2 with alkali (1 N NaOH). The islets isolated from the mouse pancreas are cultured in six well plate in presence of RPMI-1640 supplemented with 10% diluted extract. Six well plates are incubated in a $Co_2$ incubator at 37° C. for 15 to 30 days to see the viability integrity and attachment of the islets to the plates. The ability of mussel hydrolysate to support attachment and proliferation of AR42J cell line (pancreatic adenocarcinoma cell line) in a very low concentration (dilution 1:800 and 1:400) and in absence of FCS to maintain the viability of pancreatic acinar cells is noteworthy. 0.2 ml of extract is injected with the help of a sterilized disposable syringe to STZ induced diabetic mice to see hypoglycemic activity by using a glucometer. The chemical analysis of mussel extract was also studied and was found to contain high protein and no glucose.

It was found that the islets remained viable, intact and exhibited normal tissue architecture in presence of mussel extract for 30 days and remained in suspension without attachment for the first time indicating their non toxic nature. No fibroblast growth was seen from the islet indicating inhibition of fibroblast growth making them suitable for transplantation. Moreover, in the absence of foetol calf serum (FCS) and in presence of mussel hydrolysate, islets remained viable for a period of 30 days indicating importance of mussel hydrolysate as a substitute for FCS.

The injection of mussel hydrolysate into the STZ diabetic mice (experimental diabetic mice) resulted into decrement of blood glucose level from 450 mg/100 ml to 180 mg 100/ml indicating their hypoglycemic activity (Table 1).

TABLE 1

Effect of Mussel Hydrolysate on islet viability

| | % viability in presence of Green Mussel Hydrolysate | |
|---|---|---|
| Days | With FCS | Without FCS |
| 15 | 97.2% islets are alive | 97.8% islets are alive |
| 30 | 98.3% islets are alive | 98.1% islets are alive |

Viability testing done using trypan blue

Results

It was found that the islets remained viable, intact with normal tissue architecture in presence of mussel extract for 30 days and remained in suspension without attachment for the first time indicating their non-toxic nature. Non fibroblast growth was seen from the islet indicating inhibition of fibroblast growth making them suitable for transplantation. The injection of mussel hydrolysate into the STZ diabetic mice (experimental diabetic mice) resulted into decrement of blood glucose level from 450 mg/100 ml to 18 mg 100/ml indicating their hypoglycemic activity.

The daily administration of the mussel extract into the diabetic mice for a month resulted into restoration of normoglycemia exhibiting blood glucose levels comparable to non-diabetic controls (130 mg/100 ml of blood).

Advantages

1. Cultivation of islets without the use of conventional foetal calf serum.
2. No growth of fibroblast in presence of mussel hydrolysate indicating their suitability for islet transplantation.
3. Demonstration of hypoglycemic activity of the mussel hydrolysate.
4. Indication of pancreatic regeneration and reversal of diabetes.

Reference

1: Rosenberg L. and Vinik, A. I 1989, Induction of endocrine cell differentiation: A new approach to management of diabetes *J. Lab. Clin. Med.*, 114: 75–83.
2: Rosenberg, L. Duguid, W. P. Healy, M. Clas, D. and Vinik, A. I. 1992. Reversal of diabetes by the induction of islet cell neogenesis. *Transplant. Proc.*, 24: 1027–1028.
3: Hardikar, A. A. and Bhonde, R. R., 1999, Modulating experimental diabetes by treatment with cytosolic extract from the regenerating pancreas. *Diabet. Res. Clin. Pract.*, 46: 203–211.

We claim:

1. A method for treatment of a patient with Diabetes mellitus comprising administering a pharmaceutically effective amount of a mussel extract to the patient, said mussel extract being a hydrolysate of meat and mantle fluid from *Perna viridis*.

2. The method according to claim 1, wherein the hydrolysate is produced by a process comprising the steps of
   (a) extracting the meat and mantle fluid from *Perna viridis;*
   (b) fermenting the meat and mantle fluid extracted in step (a) to form a fermented extract;

(c) distillation and digestion of the fermented extract with an acid; and (d) neutralizing the distilled and digested fermented extract with an alkali.

3. The method according to claim 2, wherein the hydrolysate is produced by a process consisting essentially of the steps (a)–(d).

4. The method according to claim 1, wherein the hydrolysate is produced by a process comprising the steps of extracting the meat and mantle fluid from *Perna viridis*, diluting the extract with PBS to form a diluted extract, and adjusting the pH of the diluted extract to 7.2.

5. The method according to claim 4, wherein the extract is diluted by 50 times with 1×PBS prior to the adjusting step.

6. The method according to claim 1, wherein the mussel extract is administered to the patient in an amount effective to lower a blood glucose level in the patient.

7. The method according to claim 2, wherein the mussel extract is administered to the patient in an amount effective to restore normal blood glucose levels in the patient.

8. The method according to claim 1, wherein the hydrolysate has a high protein content and contains no glucose.

9. A method for treating and testing a subject having Diabetes mellitus comprising the steps of (a) providing a mussel extract comprising meat and mantle fluid of *Perna viridis* that has been diluted with PBS and neutralized;

(b) administering to the subject the mussel extract in a pharmaceutically effective amount to affect a blood glucose level of the subject; and (c) testing the subject to ascertain an effect of the administering of the neutralized extract.

10. The method according to claim 9, comprising the step of adding the neutralized extract provided in step (a) to an islet culture of the subject prior to said stop (b).

11. The method according to claim 10, wherein the subject is an STZ diabetic mouse.

12. The method according to claim 9, wherein the mussel extract provided in step (a) has been diluted with 1×PBS by 50 times.

13. The method according to claim 9, wherein the mussel extract provided in step (a) has been neutralized with 1 N NaOH to a pH of 7.2.

14. The method according to claim 9, wherein the testing in step (c) comprises an examination of the blood glucose level of the subject.

15. The method according to claim 9, wherein the testing in step (c) comprises an examination of beta-cell apoptis in the subject.

16. The method according to claim 10, wherein the islet culture is isolated from a mouse pancreas and is cultured in a well plate in the presence of RPMI-1640 supplemented with 10% of the diluted and neutralized extract.

17. The method according to claim 16, wherein the well plate is incubated in a $CO_2$ incubator at 37° C. for 15 to 30 days and is examined to determine viability, integrity and attachment of the islet culture to the plate.

18. The method according to claim 10, wherein the mussel extract provided in step (a) is a mussel hydrolysate that supports attachment and proliferation of a pancreatic adenocarcinoma cell line in a dilution of between 1:800 and 1:400 and in the absence of foetal calf serum.

19. The method according to claim 10, wherein the mussel extract provided in step (a) is a mussel hydrolysate that maintains a viability of pancreatic acinar cells.

20. The method according to claim 11, wherein the administering in step (b) comprises injecting the mussel extract into the mouse with the aid of a sterilized syringe.

21. The method according to claim 11, wherein the testing in step (c) comprises determining a blood glucose level of the mouse with a glucometer and comparing the blood glucose level so determined with a blood glucose level of an untreated mouse.

* * * * *